(12) United States Patent
Trieu

(10) Patent No.: US 8,216,276 B2
(45) Date of Patent: Jul. 10, 2012

(54) INTERSPINOUS SPACER

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 464 days.

(21) Appl. No.: 12/511,227

(22) Filed: Jul. 29, 2009

(65) Prior Publication Data
US 2009/0292315 A1 Nov. 26, 2009

Related U.S. Application Data

(62) Division of application No. 10/851,889, filed on May 21, 2004, now Pat. No. 7,585,316.

(51) Int. Cl.
A61B 17/70 (2006.01)
(52) U.S. Cl. ........................................................ 606/248
(58) Field of Classification Search .................... 606/60, 606/246–249; 623/17.11
See application file for complete search history.

(56) References Cited

U.S. PATENT DOCUMENTS

| | | | |
|---|---|---|---|
| 2,677,369 A | 5/1954 | Knowles | |
| 3,648,691 A | 3/1972 | Lumb et al. | |
| 4,011,602 A | 3/1977 | Rybicki et al. | |
| 4,257,409 A | 3/1981 | Bacal et al. | |
| 4,554,914 A | 11/1985 | Kapp et al. | |
| 4,573,454 A | 3/1986 | Hoffman | |
| 4,604,995 A | 8/1986 | Stephens et al. | |
| 4,657,550 A | 4/1987 | Daher | |
| 4,686,970 A | 8/1987 | Dove et al. | |
| 4,827,918 A | 5/1989 | Olerud | |
| 4,863,476 A | 9/1989 | Shepperd | |
| 4,931,055 A | 6/1990 | Bumpus et al. | |
| 5,011,484 A | 4/1991 | Breard | |
| 5,047,055 A | 9/1991 | Bao et al. | |
| 5,059,193 A | 10/1991 | Kuslich | |
| 5,092,866 A | 3/1992 | Breard et al. | |
| 5,098,433 A | 3/1992 | Freedland | |
| 5,171,278 A | 12/1992 | Pisharodi | |
| 5,201,734 A | 4/1993 | Cozad et al. | |
| 5,306,275 A | 4/1994 | Bryan | |
| 5,360,430 A | 11/1994 | Lin | |
| 5,366,455 A | 11/1994 | Dove | |
| 5,390,683 A | 2/1995 | Pisharodi | |
| 5,395,370 A | 3/1995 | Muller et al. | |
| 5,415,661 A | 5/1995 | Holmes | |
| 5,437,672 A | 8/1995 | Alleyne | |

(Continued)

FOREIGN PATENT DOCUMENTS

DE 2821678 A1 11/1979

(Continued)

OTHER PUBLICATIONS

"Dispositivo Intervertebrale Ammortizzante DIAM," date unknown, p. 1.

(Continued)

Primary Examiner — Kevin T Truong
Assistant Examiner — Michael Araj

(57) ABSTRACT

An interspinous spacer implant includes first, second, third, and fourth arms that are divided into pairs that are relatively rotatable. In an insertion configuration, the first and third arms are disposed close together, and the second and fourth arms are disposed close together. Relatively rotating the arm pairs results in a deployed configuration where the first and fourth arms are disposed close together and the second and third arms are disposed close together, with each set of arms forming a respective saddle for receiving a corresponding spinous process. Related methods are also described.

14 Claims, 9 Drawing Sheets

U.S. PATENT DOCUMENTS

| | | |
|---|---|---|
| 5,454,812 A | 10/1995 | Lin |
| 5,496,318 A | 3/1996 | Howland et al. |
| 5,518,498 A | 5/1996 | Lindenberg et al. |
| 5,554,191 A | 9/1996 | Lahille et al. |
| 5,609,634 A | 3/1997 | Voydeville |
| 5,609,635 A | 3/1997 | Michelson |
| 5,628,756 A | 5/1997 | Barker, Jr. et al. |
| 5,645,599 A | 7/1997 | Samani |
| 5,665,122 A | 9/1997 | Kambin |
| 5,674,295 A | 10/1997 | Ray et al. |
| 5,676,702 A | 10/1997 | Ratron |
| 5,690,649 A | 11/1997 | Li |
| 5,702,455 A | 12/1997 | Saggar |
| 5,707,390 A | 1/1998 | Bonutti |
| 5,716,416 A | 2/1998 | Lin |
| 5,810,815 A | 9/1998 | Morales |
| 5,836,948 A | 11/1998 | Zucherman et al. |
| 5,860,977 A | 1/1999 | Zucherman et al. |
| 5,976,186 A | 11/1999 | Bao et al. |
| 6,022,376 A | 2/2000 | Assell et al. |
| 6,048,342 A | 4/2000 | Zucherman et al. |
| 6,068,630 A | 5/2000 | Zucherman et al. |
| 6,123,731 A | 9/2000 | Boyce et al. |
| 6,126,689 A | 10/2000 | Brett |
| 6,127,597 A | 10/2000 | Beyar et al. |
| 6,132,464 A | 10/2000 | Martin |
| 6,190,414 B1 | 2/2001 | Young |
| 6,206,923 B1 | 3/2001 | Boyd et al. |
| 6,214,050 B1 | 4/2001 | Huene |
| 6,293,949 B1 | 9/2001 | Justis et al. |
| 6,352,537 B1 | 3/2002 | Strnad |
| 6,364,883 B1 | 4/2002 | Santilli |
| 6,375,682 B1 | 4/2002 | Fleischmann et al. |
| 6,402,750 B1 | 6/2002 | Atkinson et al. |
| 6,419,704 B1 | 7/2002 | Ferree |
| 6,440,169 B1 | 8/2002 | Elberg et al. |
| 6,451,019 B1 | 9/2002 | Zucherman et al. |
| 6,478,796 B2 | 11/2002 | Zucherman et al. |
| 6,520,967 B1 | 2/2003 | Cauthen |
| 6,520,991 B2 | 2/2003 | Huene |
| 6,527,806 B2 | 3/2003 | Ralph et al. |
| 6,554,833 B2 | 4/2003 | Levy |
| 6,582,433 B2 | 6/2003 | Yun |
| 6,582,467 B1 | 6/2003 | Teitelbaum et al. |
| 6,626,944 B1 | 9/2003 | Taylor |
| 6,645,207 B2 | 11/2003 | Dixon et al. |
| 6,685,742 B1 | 2/2004 | Jackson |
| 6,695,842 B2 | 2/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,534 B2 | 5/2004 | Sherman |
| 6,736,818 B2 | 5/2004 | Perren et al. |
| 6,758,863 B2 | 7/2004 | Estes et al. |
| 6,761,720 B1 | 7/2004 | Senegas |
| 6,835,205 B2 | 12/2004 | Atkinson et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,081,120 B2 | 7/2006 | Li et al. |
| 7,087,083 B2 | 8/2006 | Pasquet et al. |
| 7,097,648 B1 | 8/2006 | Globerman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,442,208 B2 | 10/2008 | Mathieu et al. |
| 7,445,637 B2 | 11/2008 | Taylor |
| 2002/0099377 A1 | 7/2002 | Zucherman et al. |
| 2002/0116000 A1 | 8/2002 | Zucherman et al. |
| 2002/0143331 A1 | 10/2002 | Zucherman et al. |
| 2002/0151895 A1 | 10/2002 | Soboleski et al. |
| 2003/0153915 A1 | 8/2003 | Nekozuka et al. |
| 2004/0097931 A1 | 5/2004 | Mitchell |
| 2004/0133204 A1 | 7/2004 | Davies |
| 2004/0167625 A1 | 8/2004 | Beyar et al. |
| 2004/0260397 A1 | 12/2004 | Lambrecht et al. |
| 2005/0010293 A1 | 1/2005 | Zucherman et al. |
| 2005/0049708 A1 | 3/2005 | Atkinson et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0228391 A1 | 10/2005 | Levy et al. |
| 2005/0261768 A1 | 11/2005 | Trieu |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0264938 A1 | 11/2006 | Zucherman et al. |
| 2006/0271044 A1 | 11/2006 | Petrini et al. |
| 2006/0293662 A1 | 12/2006 | Boyer, II et al. |
| 2007/0151116 A1 | 7/2007 | Malandain |
| 2007/0282443 A1 | 12/2007 | Globerman et al. |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1138268 A1 | 10/2001 |
| EP | 1330987 | 7/2003 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 27996640 | 4/2001 |
| FR | 2816197 A1 | 5/2002 |
| JP | 02-224660 | 9/1990 |
| JP | 09-075381 | 3/1997 |
| SU | 988281 | 1/1983 |
| WO | WO 94/26192 | 11/1994 |
| WO | WO 94/26195 | 11/1994 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/015646 | 2/2003 |
| WO | WO 03/057055 | 7/2003 |
| WO | WO 2004/047689 A1 | 6/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |

| | | | |
|---|---|---|---|
| WO | WO 2005/110258 A1 | 11/2005 | |
| WO | WO 2007/034516 A1 | 3/2007 | |
| WO | WO 2004/047691 A1 | 6/2007 | |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine " date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertebral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Instability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring—Bone Grafting for Spondylolysis and Spondylolisthesis," SPINE, 1989, pp. 455-460, vol. 14 No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, Vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Muller, "Restauration Dynamique de la Stabilité Rachidienne." Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfo. "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Stenoses du Canal Lombaire," Revue de Chirurgie Orthopedique, 1988, pp. 15-22.

Senegas et al., "Stabilisation Lombaire Souple," Instabilité Vertébrates Lombaires, Gastambide, ed., 1995, pp. 122-132, Expansion Scientifique Française, Paris, France.

Senegas, "La Ligamentoplastie Inter Vertébrale Lombaire, Alternative à L'Arthrodèse," La Revue de Medécine Orthopédique, Jun. 1990, pp. 33-35, No. 20.

Senegas, "La Ligamentoplastie Intervertébrale, Alternative a L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec. "DIAM—Modified CAD Geometry and Meshing," date unknown.

Taylor et al., "Analyse d'unc expérience clinique d'un implant postérieur amortissant," Rachis Revue de Pathologic Vertébrate, Oct./Nov. 1999. vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber,"International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èines journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist. ed., Mar.-Apr. 1976,, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

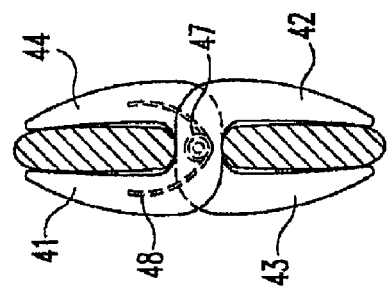
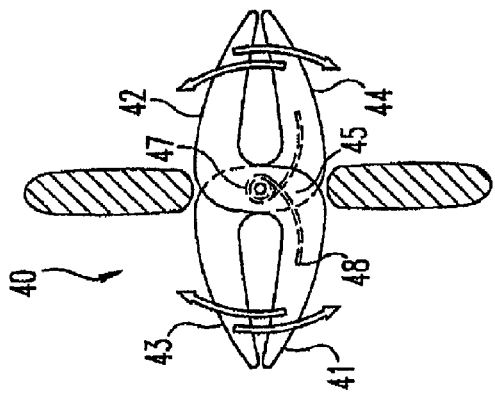
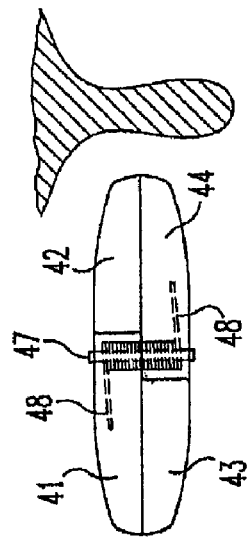
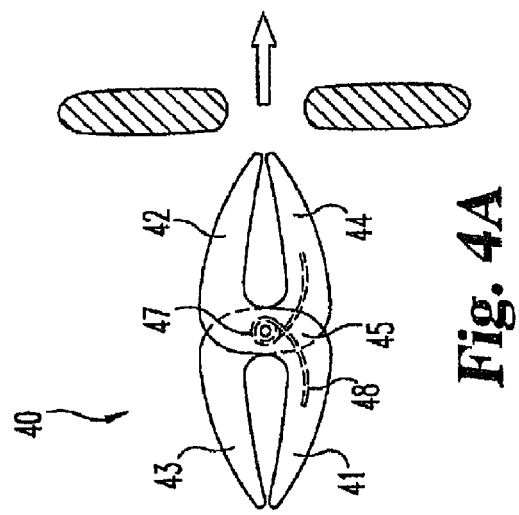

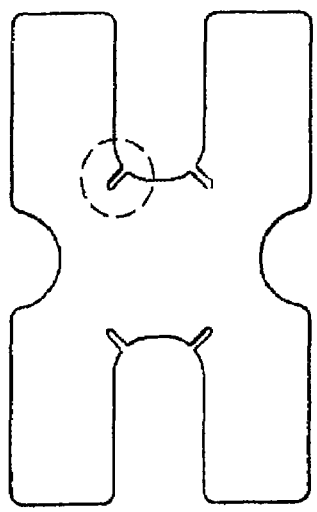
Fig. 8A
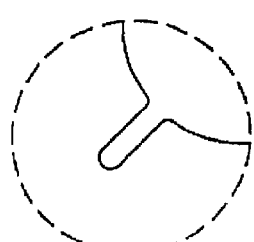  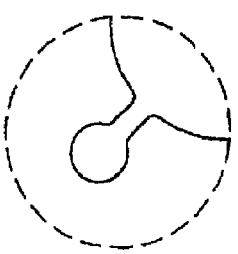  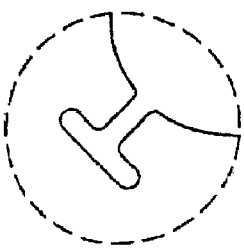  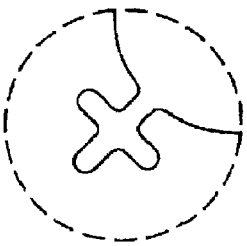
Fig. 8B   Fig. 8C   Fig. 8D   Fig. 8E
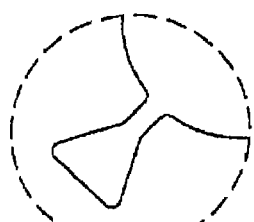    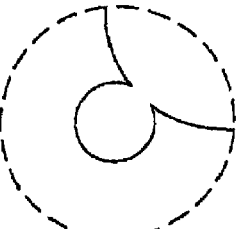  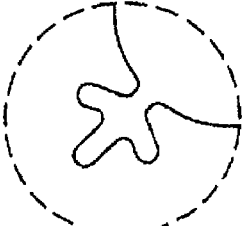
Fig. 8F   Fig. 8G   Fig. 8H   Fig. 8I
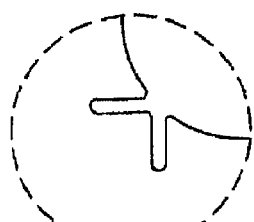  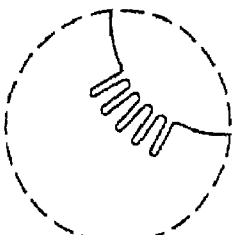  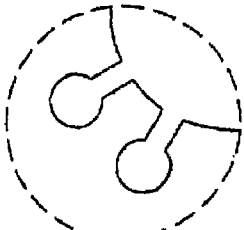  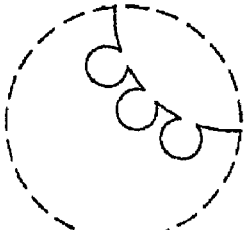
Fig. 8J   Fig. 8K   Fig. 8L   Fig. 8M

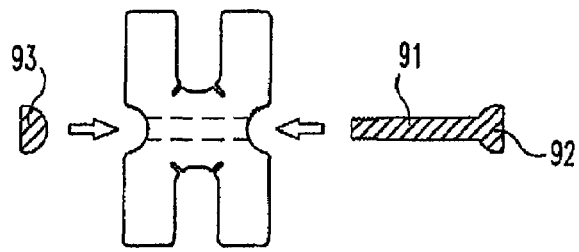
*Fig. 9A*
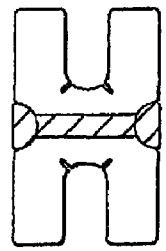
*Fig. 9B*
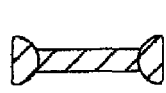 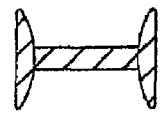 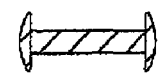 
*Fig. 10A*   *Fig. 10B*   *Fig. 10C*   *Fig. 10D*
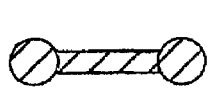   
*Fig. 10E*   *Fig. 10F*   *Fig. 10G*   *Fig. 10H*
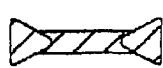 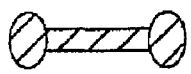 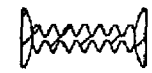
*Fig. 10I*   *Fig. 10J*   *Fig. 10K*

INTERSPINOUS SPACER

This application is a divisional of prior application Ser. No. 10/851,889, filed May 21, 2004, the entirety of which is incorporated herein by reference.

FIELD OF THE INVENTION

The present invention relates generally to devices for treating spinal stenosis, and more particularly to interspinous spacers that can be implanted in a minimally invasive manner to treat spinal stenosis.

BACKGROUND OF THE INVENTION

Lumbar spinal stenosis ("LSS"), and sometimes called sciatica) is a condition of the spine characterized by a narrowing of the lumbar spinal canal. With spinal stenosis, the spinal canal narrows and pinches the spinal cord and nerves, causing pain in the back and legs. It is estimated that approximately 5 in 10,000 people develop LSS each year. For patients who seek the aid of a physician specialist for back pain, approximately 12-15% are diagnosed as having LSS.

Several causes of spinal stenosis have been identified, including aging, heredity, arthritis, and changes in blood flow to the lower spine. Aging is believed to be the most common cause, because as a person ages the ligaments connecting the bones of the spine can thicken and spurs may develop on the bones and into the spinal canal. The cushioning discs between the vertebrae also frequently deteriorate, and the facet joints may begin to break down. Heredity is believed to play a role in some cases because it may cause some people to have a smaller than average spinal canal, typically leading to LSS symptoms even at a relatively young age.

The most common symptoms of spinal stenosis are pain and difficulty when walking, although numbness, tingling, hot or cold feelings in the legs, and weakness or tiredness may also be experienced. In extreme cases spinal stenosis can cause cauda equina syndrome, a syndrome characterized by neuromuscular dysfunction that may result in permanent nerve damage.

Common treatments for LSS include physical therapy (including changes in posture), medication, and occasionally surgery. Changes in posture and physical therapy may be effective in flexing the spine to enlarge the space available to the spinal cord and nerves—thus relieving pressure on pinched nerves. Medications such as NSAIDS and other anti-inflammatory medications are often used to alleviate pain, although they are not typically effective at addressing the cause of the pain. Surgical treatments are more aggressive than medication or physical therapy, but in appropriate cases surgery may be the best way to achieve a lessening of the symptoms associated with LSS.

The most common surgery for treating LSS is decompressive laminectomy, in which the lamina of one or more vertebrae is removed to create more space for the nerves. The intervertebral disc may also be removed, and the vertebrae may be fused to strengthen unstable segments. The success rate of decompressive laminectomy has been reported to be in excess of 65%, with a significant reduction in LSS symptoms being achieved in many cases.

More recently, a second surgical technique has been developed in which the vertebrae are distracted and an interspinous spacer is implanted to maintain the desired separation between the segments. This technique is somewhat less invasive than decompressive laminectomy, but may provide significant benefits to patients experiencing LSS symptoms.

As with other surgeries, one consideration when performing surgery to implant an interspinous spacer is the size of the incision that is required to allow introduction of the device. Minimally invasive techniques are generally preferred, but the interspinous spacers previously known to the art did not work well with minimally invasive surgical techniques. The implantation profile presented by known spacers precludes introduction through a very small incision.

A need therefore exists for an interspinous spacer that can be implanted using minimally invasive surgical techniques. The present invention addresses that need.

SUMMARY OF THE INVENTION

Briefly describing one aspect of the present invention, there is provided an interspinous spacer that is configurable to a first, collapsed configuration, and a second, expanded configuration. The spacer may be implanted in a minimally invasive manner due to the reduced profile of the collapsed configuration of the spacer.

The present invention also provides a method of introducing an interspinous spacer between adjacent spinous processes. The method preferably comprises: (a) providing a spacer that is configurable to a collapsed configuration and to an expanded configuration; wherein said collapsed configuration presents an implantation profile that is at least 10% smaller than the corresponding profile when the spacer is in its expanded configuration; (b) causing said spacer to assume its collapsed configuration; (c) introducing said spacer into a medical patient while the spacer is in its collapsed configuration; and (d) allowing the spacer to assume its expanded configuration while in the medical patient. At the conclusion of the method the expanded-configuration spacer is positioned between adjacent spinous processes.

In one aspect of the invention the spacer comprises a blocking member and four arms extending therefrom. Accordingly, the spacer may have an "H"-shaped configuration when in a relaxed configuration, and an "I"-shaped configuration when in a collapsed configuration. The method of implanting such a spacer may comprise: (a) collapsing the spacer to its "I"-shaped configuration; (b) putting the collapsed spacer in a cannula to facilitate implantation in a medical patient; (c) from an oblique posterior approach positioning the distal end of the cannula in a medical patient so that the end of the cannula clears each of a pair of adjacent spinal processes; (d) pushing the collapsed spacer through the cannula until two of the arms exit the cannula and position themselves longitudinally beside the adjacent spinal processes; and (f) withdrawing said cannula while allowing or causing the spacer to continue through the cannula such that the spacer exits the cannula and the remaining two arms are positioned longitudinally on the other side of the adjacent spinal processes.

Objects and advantages of these and other aspects of the claimed invention will be apparent from the following description.

BRIEF DESCRIPTION OF THE DRAWINGS

FIGS. 4A-4D show an interspinous spacer according to another preferred embodiment of the present invention.

FIGS. 8A-8M show representative configurations of an interspinous spacer according to other preferred embodiments of the present invention.

FIGS. 9A-9B show the use of a spacer/stabilizer, according to one preferred embodiment of the present invention.

FIGS. 10A-10K show alternative spacers/stabilizers, according to other preferred embodiments of the present invention.

DESCRIPTION OF THE PREFERRED EMBODIMENTS

Figure 1A:
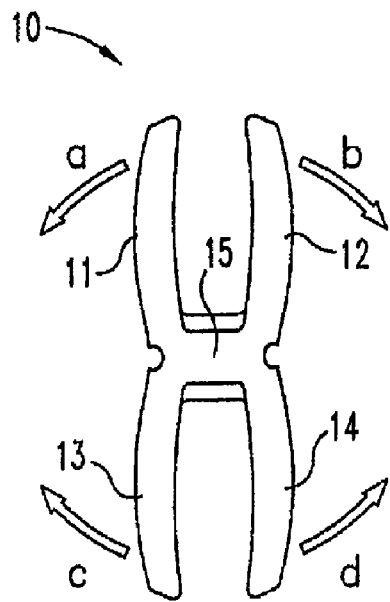
FIGS. 1A-1C show an interspinous spacer according to one preferred embodiment of the present invention.

For the purposes of promoting an understanding of the principles of the invention, reference will now be made to certain preferred embodiments and specific language will be used to describe the same. It will nevertheless be understood that no limitation of the scope of the invention is thereby intended, such alterations and further modifications in the preferred embodiments being contemplated as would normally occur to one skilled in the art to which the invention relates.

As indicated above, one aspect of the present invention relates to a method of providing an interspinous spacer between adjacent spinous processes. The method may be accomplished by: (a) providing a spacer that is configurable to a collapsed configuration and to an expanded configuration; wherein the collapsed configuration presents an implantation profile that is at least 10% smaller than the corresponding profile when the spacer is in its expanded configuration; (b) causing the spacer to assume its collapsed configuration; (c) introducing the spacer into a medical patient while the spacer is in its collapsed configuration; and (d) allowing the spacer to assume its expanded configuration while in the medical patient. At the conclusion of the method the expanded-configuration spacer is positioned between adjacent spinous processes.

As to the characteristics of the spacer generally, the spacer is designed to maintain a minimal distance between the spinous processes of adjacent vertebrae. As such, the spacer typically has a blocking portion that keeps the vertebrae from coming together. In general, the blocking portion maintains a distance of ¼" to ½" between the spinous processes.

Additionally, the spacer is preferably designed to fit snugly around the spinous processes, and thus to avoid being dislodged by movement of the spine. In one embodiment the spacer accomplishes that end by including "arms" extending from the blocking portion upward along both sides of the upper spinous process, and "arms" extending from the blocking portion downward along both sides of the lower spinous process. The arms keep the spacer from moving laterally with respect to the spinous processes. In some embodiments the arms have a relaxed configuration such that the distance between opposing arms is slightly less than width of a spinous process at that point. Thus, the arms will grip the spinous process to provide additional stability to the implanted spacer.

In one aspect of the invention the spacer comprises a blocking member with four arms extending therefrom. Accordingly, the spacer may have an "H"-shaped configuration when in a relaxed configuration, and an "I"-shaped configuration when in a collapsed configuration. The method of implanting such a spacer may comprise: (a) collapsing the spacer to its "I"-shaped configuration; (b) putting the collapsed spacer in a cannula to facilitate implantation in a medical patient; (c) from an oblique posterior approach positioning the distal end of the cannula in a medical patient so that the end of the cannula clears each of a pair of adjacent spinal processes; (d) pushing the collapsed spacer through the cannula until two of the arms exit the cannula and position themselves longitudinally beside the adjacent spinal processes; and (f) withdrawing said cannula while allowing or causing the spacer to continue through the cannula such that the spacer exits the cannula and the remaining two arms are positioned longitudinally on the other side of the adjacent spinal processes.

In one embodiment the spacer is collapsible by virtue of the fact that the material used to make the spacer is very elastic and pliable. In such embodiments the spacer arms may be manipulated so as to transform the H-shaped configuration to an I-shaped configuration merely by bending the arms from an orientation that is generally perpendicular to the crossbar of the "H" to an orientation that is generally parallel to the crossbar of the "H." Accordingly, in one embodiment the H-shaped implant is converted to an I-shaped implant by folding the upwardly and downwardly extending arms so that they extend horizontally, i.e., the folded arms extend in a direction that is generally parallel to the crossbar of the "H." When the force manipulating the spacer arms is released, the arms then return to their original orientation that is generally perpendicular to the crossbar of the "H." FIGS. 1A-1C, described below, show the manipulation of one H-shaped embodiment.

In another embodiment the spacer is collapsible by virtue of a pivot point near the center of the spacer. Such embodiments may work much like a pair of scissors, with four arms extending from a central pivot. As with scissors, the device may be converted from a generally "X"-shaped device to a generally "I"-shaped device by pivoting one pair of arms relative to the other. FIGS. 4A-4C, described below, show one such pivoting embodiment.

The ability of the spacer to assume a collapsed configuration allows the spacer to be implanted using a minimally invasive surgical technique. Most preferably, the surgery is accomplished using a posterior oblique approach through a small incision in the patient's back.

Regardless of the surgical approach used for implantation, when the spacer passes into the body it presents an "implantation profile" corresponding to the size of the implant as it passes through the plane of the opening in the body. The implantation profile therefore defines the size of the opening required to accept the implant. While it is appreciated that different surgeons may use different orientations of a spacer when implanting it into a patient, there is generally one orientation that presents a smaller implantation profile than the others. For the purposes of this disclosure then, the term implantation profile is used to identify the size of an implant as it passes through an opening in the body, given that the implant is manipulated so as to present the smallest possible implantation profile. To the extent the size of the portion of the implant that is passing through the opening increases or decreases as different portions of the implant pass through the opening, the implantation profile is the maximum size presented to the opening during implantation, and therefore corresponds to the minimum opening size required to accommodate the implant.

In one embodiment of the present invention the implantation profile is at least about 10% smaller than the corresponding profile when the spacer is in its expanded configuration. In other embodiments the implantation profile is at least about 20% smaller than the corresponding profile when the spacer is in its expanded configuration. More preferably, the implantation profile is about 25% smaller than the corresponding profile when the spacer is in its expanded configuration. Most preferably, the implantation profile is at least 50% smaller than the corresponding profile when the spacer is in its expanded configuration.

An interspinous spacer for use in the invention may be formed from a wide variety of biocompatible materials that can undergo reversible elastic deformation. Examples of such materials include elastic or rubbery polymers, hydrogels or other hydrophilic polymers, or composites thereof. Particularly suitable elastomers include silicone, polyurethane, copolymers of silicone and polyurethane, polyolefins, such as polyisobutylene and polyisoprene, neoprene, nitrile, vulcanized rubber and combinations thereof.

Examples of polyurethanes include thermoplastic polyurethanes, aliphatic polyurethanes, segmented polyurethanes, hydrophilic polyurethanes, polyether-urethane, polycarbonate-urethane and silicone polyetherurethane. Other suitable hydrophilic polymers include polyvinyl alcohol hydrogel, polyacrylamide hydrogel, polyacrylic hydrogel, poly(N-vinyl-2-pyrrolidone hydrogel, polyhydroxyethyl methacrylate hydrogel, and naturally occurring materials such as collagen and polysaccharides, such as hyaluronic acid and cross-linked carboxyl-containing polysaccharides, and combinations thereof.

In other embodiments the spacer is made of a metal that can undergo reversible elastic deformation, such as shape memory metals or nickel titanium.

The nature of the materials employed to form the blocking portion of the spacer should be selected so the formed implants have sufficient load bearing capacity. In preferred embodiments, a compressive modulus of at least about 0.1 Mpa is desired, although compressive strengths in the range of about 1 Mpa to about 20 Mpa are more preferred. Most preferably the compressive modulus is at least about 5 Mpa.

In some embodiments the spacer may also advantageously deliver desired pharmacological agents. The pharmacological agent may be a growth factor that may advantageously repair damaged tissue or bone, and may include an osteoinductive factor (e.g., a bone morphogenetic protein), transforming growth factor-ss (TGF-ss), insulin-like growth factor, platelet derived growth factor, fibroblast growth factor or other similar growth factor or combination thereof having the ability to repair tissue or bone.

In other forms of the invention, the spacer may comprise a pharmacological agent used for treating various spinal conditions, including degenerative disc disease, spinal arthritis, spinal infection, spinal tumor and osteoporosis. Such agents include antibiotics, analgesics, anti-inflammatory drugs, including steroids, and combinations thereof. Other such agents are well known to the skilled artisan. These agents are also used in therapeutically effective amounts. Such amounts may be determined by the skilled artisan depending on the specific case.

The pharmacological agents, if any, are preferably dispersed within the spacer for in vivo release. The pharmacological agents may be dispersed in the spacer by adding the agents to the spacer when it is formed, by soaking a formed spacer in an appropriate solution containing the agent, or by other appropriate methods known to the skilled artisan. In other forms of the invention, the pharmacological agents may be chemically or otherwise associated with the spacer. For example, the agents may be chemically attached to the outer surface of the spacer.

In some embodiments the device may include one of more X-ray markers such as tantalum markers to assist in positioning the implant. A combination of larger x-ray markers and smaller x-ray markers may be used to facilitate observing the orientation of the device when implanted. The x-ray markers can be more readily observed on x-rays, making the positioning and orientation of the device more easily observed and corrected.

Figure 1B:
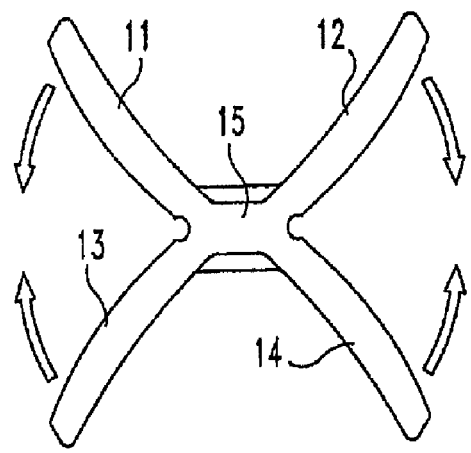
Figure 1C:
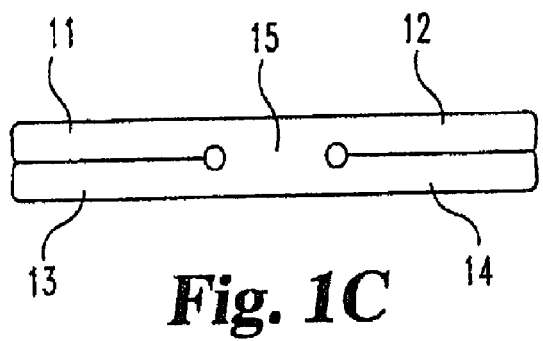

Referring now to the drawings, FIGS. 1A-C show an interspinous spacer according to one embodiment of the present invention. Spacer 10 includes a blocking member 15 and arms 11, 12, 13, and 14. When the spacer is in its relaxed (expanded) configuration as shown in FIG. 1A, it resembles an "H," with arms 11, 12, 13, and 14 being the legs of the H, and blocking member 15 being the crossbar. As illustrated in the drawing, the arms are generally perpendicular to the blocking member when the spacer is in its relaxed/expanded configuration.

To use the spacer, the arms are manipulated to be parallel to the blocking member, manipulating the spacer to its collapsed (implantable) configuration as illustrated in FIGS. 1B and 1C. The manipulation makes the spacer assume the shape of an "I" rather than the shape of an "H." Arrows a, b, c, and d, show the direction of the manipulation to transform the "H" to an "I." As indicated above, the preferred manipulation converts the H-shaped implant to an I-shaped implant by folding the upwardly and downwardly extending arms so that they extend horizontally in a direction that is generally parallel to the crossbar of the "H." When the spacer is manipulated to its collapsed/implantable configuration, the implantation profile of the profile is reduced.

Figure 2A:
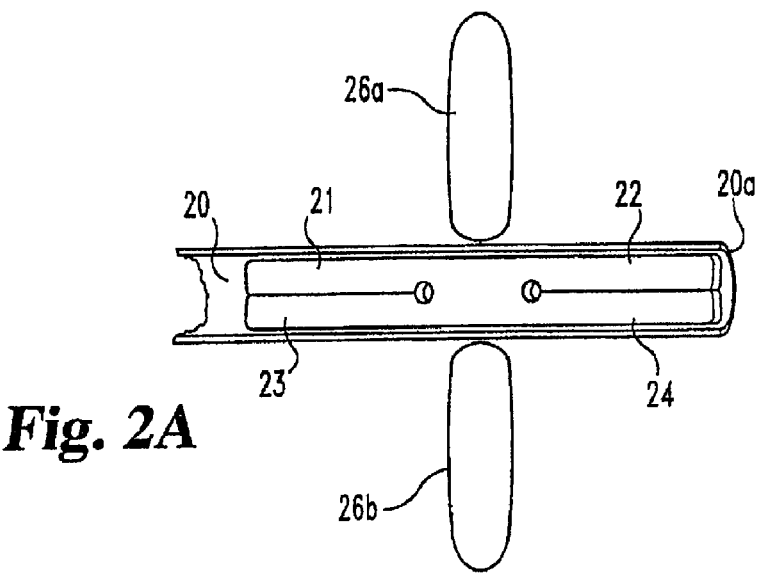
FIGS. 2A-2E show the interspinous spacer of FIG. 1 being implanted in a medical patient.

FIGS. 2A-E show one embodiment of a method for implanting the spacer. In FIG. 2A, spacer 10 is loaded in cannula 20 while the spacer is in its collapsed/implantable configuration. The spacer is in its collapsed configuration so that its implantation profile is reduced from the corresponding profile when the spacer is in its relaxed configuration.

Figure 2B:
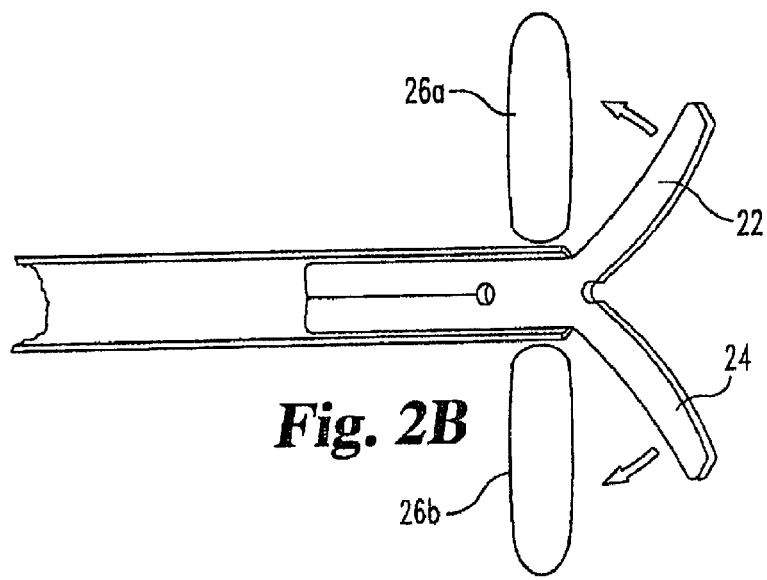
Figure 2C:
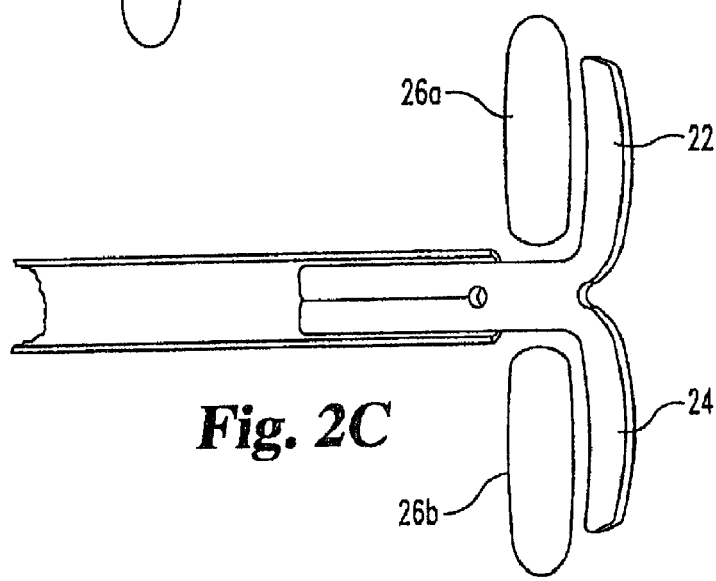

Cannula 20 is positioned between two spinous processes, with the tip 20a of the cannula extending just beyond the spinous processes when the cannula is inserted from a posterior oblique approach. When the cannula is positioned, the spacer is pushed from the cannula so that the leading pair of arms 22 and 24 begins to unfold from its collapsed/implantable configuration to its relaxed/expanded configuration, as shown in FIG. 2B. As the arms unfold they extend upward and downward along one side of two spinous processes, as shown in FIG. 2C.

Figure 2D:
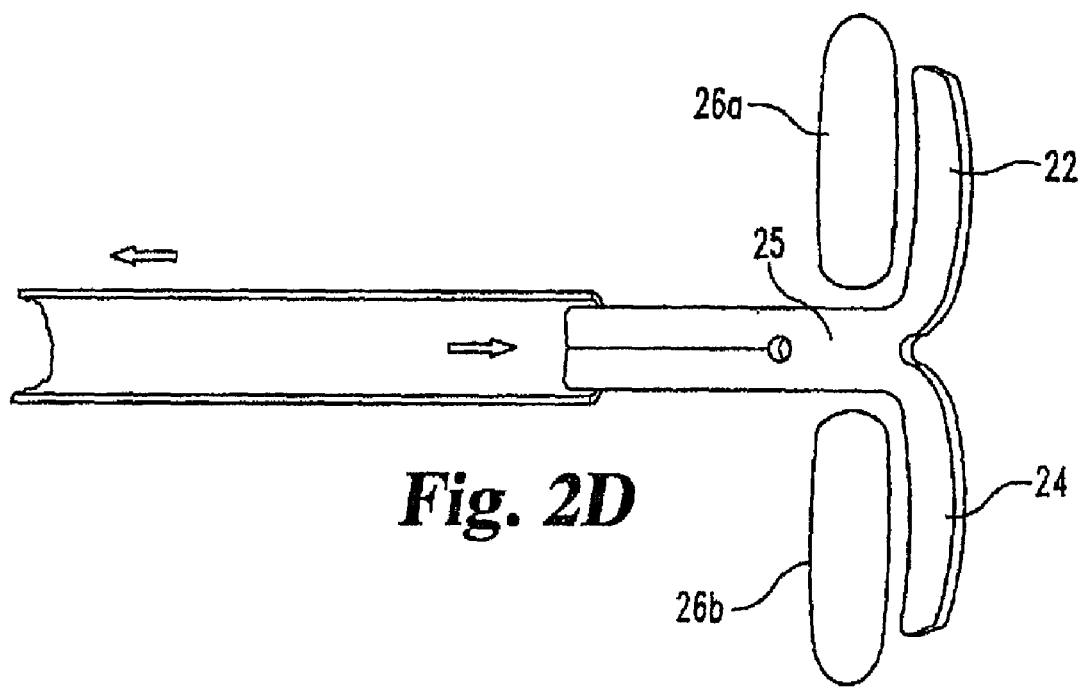
Figure 2E:
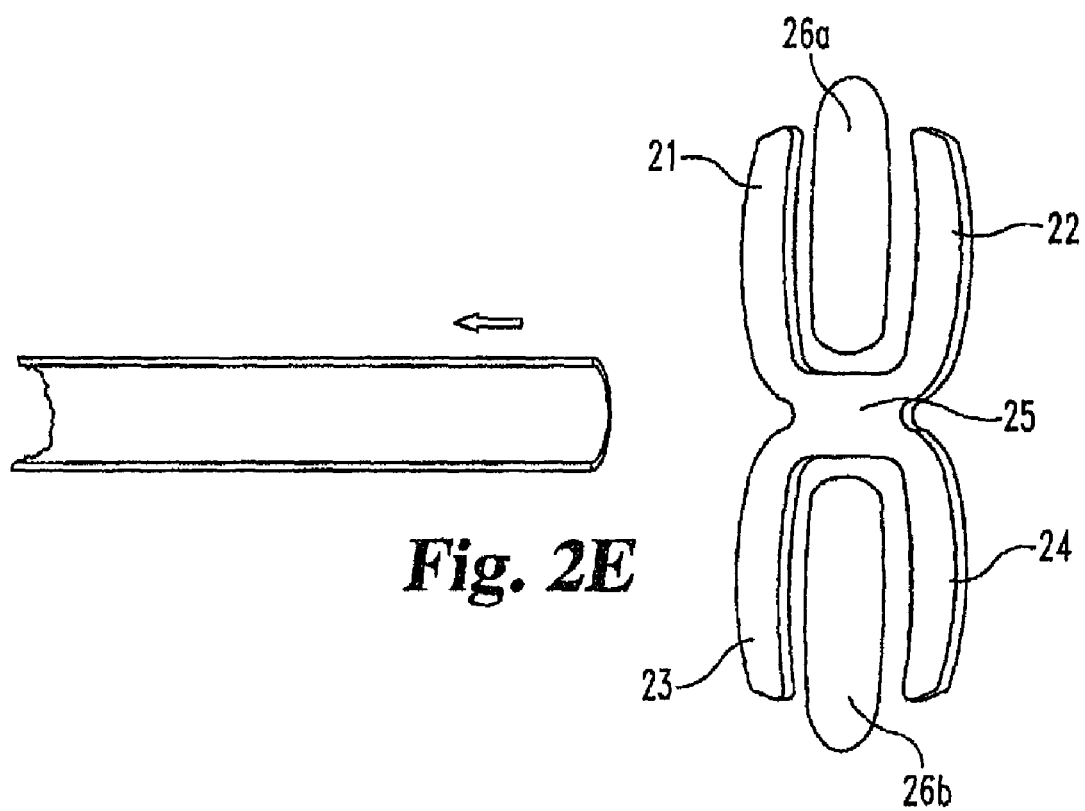

The cannula is then withdrawn as the spacer is ejected, as shown in FIG. 2D. The blocking portion 25 of spacer 10 is positioned between the two spinous processes, and the second pair of arms 21 and 23 unfolds to extend upward and downward along the second side of the spinous processes, as shown in FIG. 2E.

In another embodiment the spacer may have indents and/or other surface features to facilitate collapsing and implanting the spacer, or to avoid cracking or tearing the implant when the arms are folded to their collapsed configuration. Features such as ridges to facilitate gripping the spinous processes may also be included.

For example, FIGS. 7A through 7L show embodiments having surface features to reduce compressive forces on the outside walls during deformation (in the "I" shape). The illustrated surface features, which are merely examples of the many types and/or shapes of surface features that may be utilized, act to reduce compressive forces on the outside surface of the implant when the implant is folded from its "H" configuration to its "I" configuration.

In addition or as an alternative, surface features may be included on the "inner" surface of the implant to reduce tensile forces on those surfaces when the implant is deformed. FIGS. 8A through 8M show some preferred embodiments of such surface features. Here too, the illustrated surface features are merely examples of the many types and/or shapes of surface features that may be utilized to reduce "stretching" or tensile forces on the inside surface of the implant when the implant is folded from its "H" configuration to its "I" configuration.

Figure 3A:
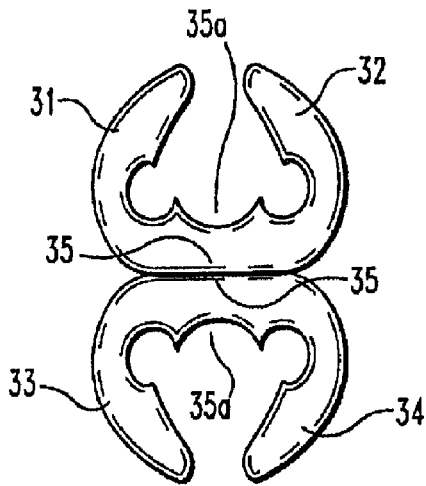
FIGS. 3A-3C show an interspinous spacer according to another preferred embodiment of the present invention.
Figure 3B:
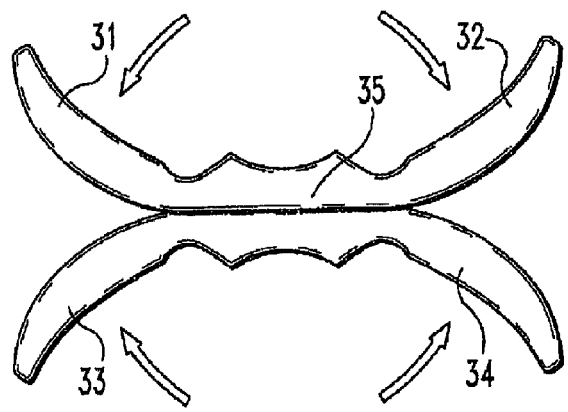
Figure 3C:
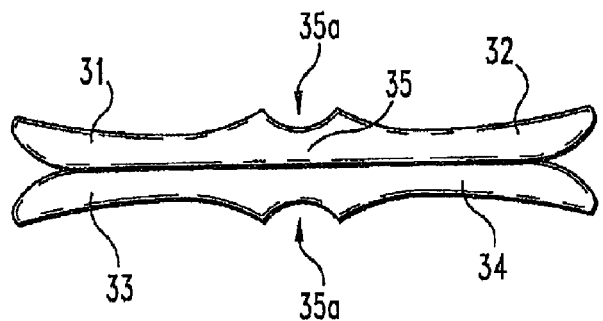

One embodiment effective to reduce both compressive and tensile forces is shown in FIGS. 3A-3C. In that embodiment, spacer 30 comprises arms 31, 32, 33, and 34, and blocking portion 35. Blocking portion 35 includes at least one indent 35a, and may include two indents as shown in FIG. 3A. The implant is manipulated from its relaxed configuration to its straightened configuration as before. Arms 31 and 32 are folded downward until they are generally horizontal and lie in the same direction as blocking member 35. Arms 32 and 34 are folded upward until they are generally horizontal and lie in the same direction as blocking member 35. The folded implant can then be placed in a cannula and pushed through a small opening in a patient's body as described above. Once implanted, the device relaxes to its H-shaped configuration with indents 35a centering the implant around the spinous processes and arms 31, 32, 33, and 34 preventing lateral displacement.

In another embodiment the implant may have one or more arms that pivot in relation to other non-pivoting arms. The arms preferable pivot around a central point in the blocking member. Most preferably, the device comprises four arms arranged as two pivoting pairs, with each of the two pairs of arms pivoting together. In the most preferred embodiments, the pivoting arms are substantially rigid, although they may be elastic in other embodiments.

FIG. 4A shows one preferred embodiment of the present invention in which the implant has pivoting arms. Pivot post 47 defines the point around which arms 41, 42, 43, and 44 pivot. In the illustrated embodiment, arms 41 and 42 form one pair, and arms 43 and 44 form another pair. A spring 48 may be used to bias the arms to their closed position, as shown in FIGS. 4A and 4B. In some embodiments spring 48 is wound at least partially around pivot post 47.

To operate implant 40, the implant is preferably allowed to adopt its closed position as shown in FIG. 4A. In this position the implant has its minimum implantation profile, allowing the closed implant to pass through a small incision in a patient. After the implant has been introduced into the patient, the implant is opened by allowing the arms to move in the direction of the arrows shown in FIG. 4C. This allows the implant to adopt its open configuration as shown in FIG. 4D. In that configuration, the implant has a profile that is larger than the profile of the implant in its closed configuration.

In some embodiments the blocking member portion of implant 40 has a concave shape when the arms are opened to their open configuration. This allows the blocking member to fit more securely around the interspinous processes.

In another embodiment of the present invention the implant includes a spacer portion between the two pair of opposing arms. The spacer portion may give the device an adjustable height, with varying sizes of rigid spacer portions being available.

Figure 5:
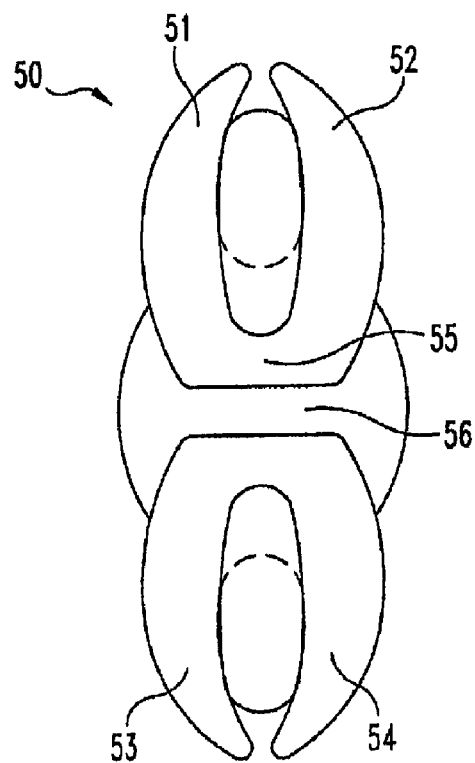
FIG. 5 shows an interspinous spacer according to another preferred embodiment of the present invention, including a rigid spacer portion to give the device an adjustable height.

FIG. 5 shows one embodiment of the device of the present invention having a spacer/stabilizer portion. In spacer 50, arms 51, 52, 53, and 54 extend from blocking portion 55 and spacer/stabilizer portion 56.

The device with a spacer is used in a manner similar to the device without a spacer. Accordingly, arms 51, 52, 53, and 54 may fold down to lie horizontally along the axis of blocking member 55 and spacer portion 56, so that the device has an implantation profile that is at least 10% smaller than the corresponding profile of the device in its relaxed configuration.

Alternative embodiments of an interspinous spacer having a spacer/stabilizer are shown in FIGS. 9A-9B, and in FIGS. 10A-10K. These embodiments are particularly effective for reducing or preventing in vivo deformation of the device, and thus for reducing or preventing dislocation and/or migration after implantation. In the embodiments illustrated in the drawings, the central shank 91 provides the spacing effect for varying desired thicknesses, while the end portions 92 and 93 provide stabilization against in vivo deformation into the "I" shape. As may be appreciated by persons skilled in the art, the illustrated spacers/stabilizers may be incorporated into the implant in vivo, with the spacer/stabilizer being installed and assembled only after the device has assumed its "H" shape.

Figure 6:
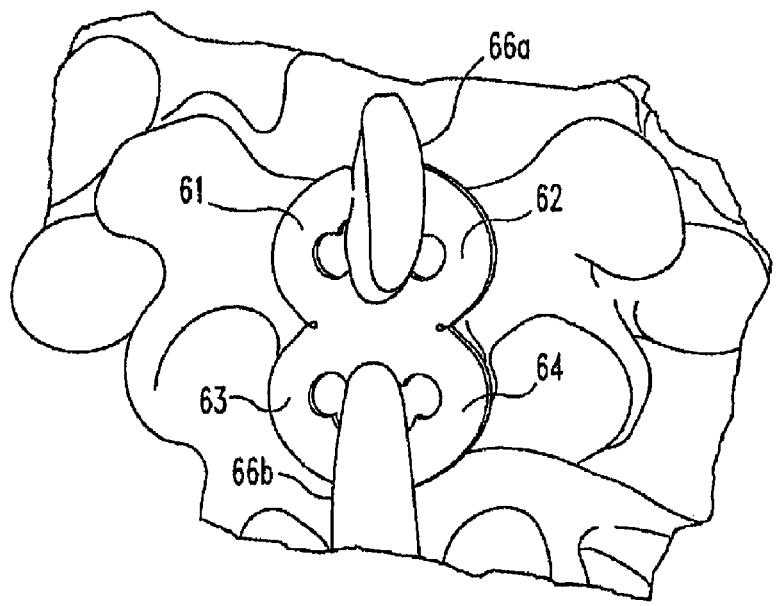
FIG. 6 shows an interspinous spacer implanted in a medical patient.
Figure 7A:
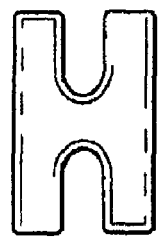
FIGS. 7A-7L show alternative shapes of an interspinous spacer according to other preferred embodiments of the present invention.
Figure 7B:
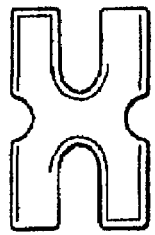
Figure 7C:
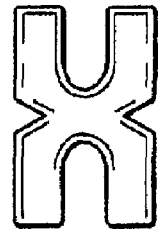
Figure 7D:
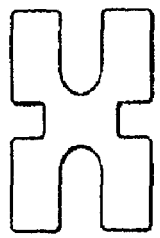
Figure 7E:
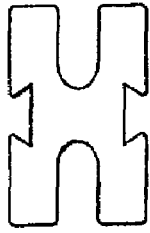
Figure 7F:
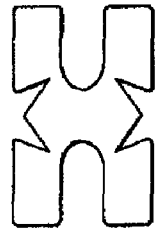
Figure 7G:
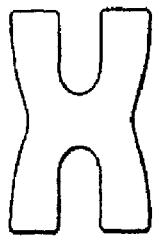
Figure 7H:
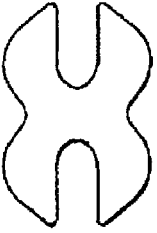
Figure 7I:
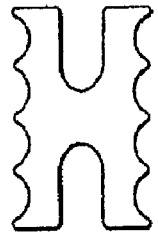
Figure 7J:
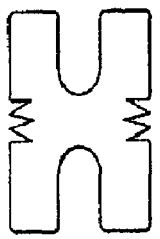
Figure 7K:
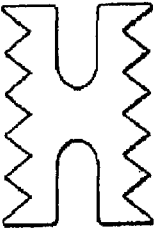
Figure 7L:
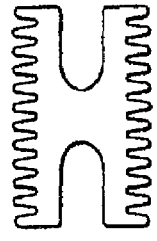

FIG. 6 shows an interspinous spacer according to one preferred embodiment of the present invention, after implantation in a medical patient. Arms 61, 62, 63, and 64 of spacer 60 grip the spinous processes 66a and 66b to hold the spacer in position.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A spinal implant comprising:
a first arm assembly comprising first and second arms and a first intermediate section disposed between and connecting the first and second arms; the first and second arms extending in generally opposite directions and the first intermediate section disposed generally transverse to the first and second arms;
a second arm assembly comprising third and fourth arms and a second intermediate section disposed between and connecting the third and fourth arms; the third and fourth arms extending in generally opposite directions and the second intermediate section disposed generally transverse to the third and fourth arms;
the implant movable from a first insertion configuration to a second deployed configuration by pivoting the second arm assembly relative to the first arm assembly about a pivot axis so that the first and second intermediate sections rotate relative to each other;
wherein, in the first configuration:
the first and third arms extend in the same general direction in spaced relation to each other;
the second and fourth arms extend in the same general direction in spaced relation to each other;
a distal tip of the first arm is disposed closer to the third arm than the fourth arm;
a distal tip of the second arm is disposed closer to the fourth arm than the third arm;
the intermediate sections of the first and second arm assemblies overlap when viewed along the pivot axis;
wherein, in the second configuration:
the first and fourth arms extend in the same general direction and form a lower saddle for receiving a first spinous process of a pair of adjacent spinous processes;

the second and third arms extend in the same general direction and form an upper saddle for receiving a second spinous process of the pair of adjacent spinous processes;
a distal tip of the first arm is disposed closer to the fourth arm than the third arm;
a distal tip of the second arm is disposed closer to the third arm than the fourth arm;
the intermediate sections of the first and second arm assemblies overlap when viewed along the pivot axis.

2. The spinal implant of claim 1 further comprising a biasing element for biasing the first arm assembly in a first rotational direction relative to the second arm assembly.

3. The spinal implant of claim 1 wherein, in the second configuration, the first and fourth arms angle toward each other.

4. The spinal implant of claim 1 wherein the first arm, the second arm, and the first intermediate section of the first arm assembly are substantially rigid.

5. The spinal implant of claim 1 wherein the first and second arms have substantially the same relative orientation in the first and second configurations; and wherein the third and fourth arms have substantially the same relative orientation in the first and second configurations.

6. The spinal implant of claim 1 wherein both the first and second arms retain the same orientation relative to the first intermediate section and relative to each other in both the first and second configurations.

7. The spinal implant of claim 6 wherein both the third and fourth arms retain the same orientation relative to the second intermediate section and relative to each other in both the first and second configurations.

8. A spinal implant comprising:
a first arm assembly comprising first and second arms and a first intermediate section disposed between and connecting the first and second arms; the first and second arms extending in generally opposite directions and the first intermediate section disposed generally transverse to the first and second arms;
a second arm assembly comprising third and fourth arms and a second intermediate section disposed between and connecting the third and fourth arms; the third and fourth arms extending in generally opposite directions and the second intermediate section disposed generally transverse to the third and fourth arms;
the implant movable from a first insertion configuration to a second deployed configuration by pivoting the second arm assembly relative to the first arm assembly about a pivot axis;
a pivot pin disposed along the pivot axis;
wherein, in the first configuration:
the first and third arms extend in the same general direction in spaced relation to each other;
the second and fourth arms extend in the same general direction in spaced relation to each other;
a distal tip of the first arm is disposed closer to the third arm than the fourth arm;
a distal tip of the second arm is disposed closer to the fourth arm than the third arm;
the intermediate sections of the first and second arm assemblies overlap when viewed along the pivot axis;
wherein, in the second configuration:
the first and fourth arms extend in the same general direction and form a lower saddle for receiving a first spinous process of a pair of adjacent spinous processes;
the second and third arms extend in the same general direction and form an upper saddle for receiving a second spinous process of the pair of adjacent spinous processes;
a distal tip of the first arm is disposed closer to the fourth arm than the third arm;
a distal tip of the second arm is disposed closer to the third arm than the fourth arm;
the intermediate sections of the first and second arm assemblies overlap when viewed along the pivot axis.

9. A spinal surgical implantation method comprising:
providing an interspinous spacer implant comprising:
a first arm assembly comprising first and second arms and an intermediate section disposed between and connecting the first and second arms; the first and second arms extending in generally opposite directions and the intermediate section disposed generally transverse to the first and second arms;
a second arm assembly comprising third and fourth arms and an intermediate section disposed between and connecting the third and fourth arms; the third and fourth arms extending in generally opposite directions and the intermediate section disposed generally transverse to the third and fourth arms;
inserting the implant between first and second adjacent spinous processes in a first insertion configuration wherein:
the first and third arms extend in the same general direction;
a distal tip of the first arm is disposed closer to the third arm than the fourth arm;
a distal tip of the second arm is disposed closer to the fourth arm than the third arm;
while the implant is disposed between the adjacent spinous processes, changing the implant from the first configuration to a second deployed configuration by pivoting the first arm assembly relative to the second arm assembly about a pivot axis; wherein, in the second configuration:
the first and fourth arms extend inferiorly and form a lower saddle that receives an inferior spinous process of the adjacent spinous processes;
the second and third arms extend superiorly and form an upper saddle that receives a superior spinous process of the adjacent spinous processes;
the intermediate sections of the first and second arm assemblies overlap when viewed along the pivot axis.

10. The method of claim 9 wherein, after the changing the implant to the second configuration, the first and third arms are disposed on a first lateral side of the adjacent spinous processes and the second and fourth arms are disposed on a second opposite lateral side of the adjacent spinous processes.

11. The method of claim 9 wherein, after the changing the implant to the second configuration:
a distal tip of the first arm is disposed closer to the fourth arm than the third arm;
a distal tip of the second arm is disposed closer to the third arm than the fourth arm.

12. The method of claim 9 further comprising biasing the first arm assembly in a first rotational direction relative to the second arm assembly.

13. The method of claim 9 further comprising introducing the spacer implant into a patient while the spacer implant is in the first configuration.

14. The method of claim 9 wherein the changing the implant from the first configuration to the second configuration comprises disposing the intermediate sections of the first and second arm assemblies so as to extend through a sagittal plane defined by the adjacent spinous processes.

* * * * *